United States Patent
Serhan et al.

(10) Patent No.: US 7,217,425 B2
(45) Date of Patent: May 15, 2007

(54) AUTOLOGOUS COATINGS FOR IMPLANTS

(75) Inventors: Hassan Serhan, South Easton, MA (US); Thomas M. DiMauro, Southboro, MA (US); Terri Kapur, Stoughton, MA (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 11/044,388

(22) Filed: Jan. 27, 2005

(65) Prior Publication Data

US 2006/0019875 A1    Jan. 26, 2006

Related U.S. Application Data

(60) Provisional application No. 60/590,526, filed on Jul. 23, 2004.

(51) Int. Cl.
*A61F 2/02* (2006.01)
*A61F 2/34* (2006.01)
*A61M 31/00* (2006.01)

(52) U.S. Cl. .................. 424/423; 514/12; 604/508; 623/13.12; 623/17.11; 623/22.11; 623/22.15

(58) Field of Classification Search ............... 424/422; 530/395; 435/334
See application file for complete search history.

(56) References Cited

U.S. PATENT DOCUMENTS

| | | |
|---|---|---|
| 3,886,948 A | 6/1975 | Hakim |
| 4,332,255 A | 6/1982 | Hakim et al. |
| 4,387,715 A | 6/1983 | Hakim et al. |
| 4,551,128 A | 11/1985 | Hakim et al. |
| 4,595,390 A | 6/1986 | Hakim et al. |
| 4,615,691 A | 10/1986 | Hakim et al. |
| 4,772,257 A | 9/1988 | Hakim et al. |
| 4,816,016 A | 3/1989 | Schulte et al. |
| 5,176,627 A | 1/1993 | Watson |
| 5,282,864 A | 2/1994 | Noiles et al. |
| 5,928,182 A | 7/1999 | Kraus et al. |
| 6,083,919 A | 7/2000 | Johnson et al. |
| 6,352,557 B1 | 3/2002 | Ferree |
| 6,419,944 B2 | 7/2002 | Tobinick |
| 6,503,507 B1 | 1/2003 | Allen |
| 6,527,759 B1 | 3/2003 | Tachibana et al. |
| 6,592,814 B2 * | 7/2003 | Wilcox et al. ............... 422/28 |
| 6,592,888 B1 | 7/2003 | Jensen et al. |
| 6,605,751 B1 | 8/2003 | Gibbins et al. |
| 2002/0026244 A1 | 2/2002 | Trieu |
| 2003/0039651 A1 | 2/2003 | Olmarker |
| 2003/0049256 A1 | 3/2003 | Tobinick |
| 2003/0125679 A1 | 7/2003 | Kubota et al. |
| 2003/0204229 A1 | 10/2003 | Stokes |
| 2005/0013836 A1 * | 1/2005 | Radd .......................... 424/400 |
| 2005/0048644 A1 | 3/2005 | Hedrick et al. |
| 2005/0170070 A1 * | 8/2005 | Layrolle et al. ............. 427/2.1 |

FOREIGN PATENT DOCUMENTS

EP         0990924       4/2000
WO    WO 02/100387 A1   12/2002

OTHER PUBLICATIONS

Duration of protective activity of cerebrospinal fluid shunt catheters impregnated with antimicrobial agents to prevent bacterial catheter-related infection. Bayston R, Lambert E. J Neurosurg. 1997; 87: 247-251.*
Lactoferrin and host defense. Ward PP, Uribe-Luna S, Conneely OM. Biochem Cell Biol. 2002; 80: 95-102. Review.*
Transforming growth factor beta is an important immunomodulatory protein for human B lymphocytes. Kehrl JH, Roberts AB, Wakefield LM, Jakowiew S, Sporn MB, Fauci AS. J Immunol. 1986; 137: 3855-3860.*
Role of IL-10 for Induction of Anemia During Inflammation. Tilg, H, Ulmer H, Kaser A, Weiss G. J. Immunol. 2002 15; 169: 2204-2209.*
Yokota et al., Adiponectin, A New Member of the Family of Soluble Defense Collagens, Negatively Regulates the Growth of Myelomonocytic Progenitors and the Functions of Macrophages, Blood, 2000, vol. 96, p. 1723-1732.*
Ardehali et al., The Inhibitory Activity of Serum to Prevent Bacterial Adhesion is Mainly Due to Apo-transferrin, J. Biomed. Mat. Res., 2003, vol. 66, pp. 21-28.*
Alini, Eur. Spine J., *A Biological Approach to Treating Disc Degeneration: Not for Today, but Maybe for Tomorrow*, 11 (Supp. 2), 2002, pp. S215-220.
Ardehali, J. Biomed., *The Inhibitory Activity of Serum to Prevent Bacterial Adhesion is Mainly Due to Apo-transferrin*, Mat. Res., Jul. 1, 2003, 66, 1, pp. 21-28.
Cassatella, J. Exp. Med. *Interleukin 10 (IL-10) Inhibits the Release of Proinflammatory Cytokines* . . . , Dec. 1, 1993, 178(6), pp. 2207-2211.
Cassatella, J. Exp. Med., *Interleukin 10 (IL-10Upregulates IL-1 Receptor Antagonist Production* . . . , May 1, 1994, 179(5) pp. 1695-1699.
Desai, Anal. Biochem., *Coated Microwell Plate-based Affinity Purification of Antigens*, May 15, 2004, 328(2), pp. 162-165.
Diez, Eur. J. Endocrinology, *The Role of the Novel Adipocyte-derived Hormone Adiponectin in Human Disease*, 2003, 148, pp. 293-300.
Goupille, Spine, *Matrix Metalloproteinases: The Clue to Intervertebral Disc Degeneration?*, 23(14), 1998, pp. 1612-1626.
Guillen, Arthritis Rheum., *The Effects of Local Administration of Lactoferrin on Inflammation in Murine Autoimmune and Infectious Arthritis*, 43, 2000, pp. 2073-2780.

(Continued)

Primary Examiner—Robert A. Wax
(74) Attorney, Agent, or Firm—Theodore Shatynski

(57) ABSTRACT

A hydrocephalus shunt having an anti-inflammatory coating applied to at least the outside surface of the ventricular catheter. Such coatings are also applicable to other medical devices or implants.

20 Claims, No Drawings

OTHER PUBLICATIONS

Hayashida, Eur. J. Pharmacology, *Lactoferin Enhances Peripheral Opioid-mediated Antinociception via Nitric Oxide in Rats*, 484, 2004, pp. 175-181.

Hayashida, J. Vet. Med. Sci., *Oral Administration of Lactoferrin Inhibits Inflammation and Nociception in Rat Adjuvant-Induced Arthritis*, 66(2), 2004, pp. 149-154.

Karppinen, Spine, *Tumor Necrosis Factor-α Monoclonal Antibody, Infliximab, Used to Manage Severe Sciatia*, 28(6), 203, pp. 750-754.

Kurnada, Circulation, *Adiponectin Specifically Increased Tissue Inhibitor of Metalloproteinase-1 Through Interleukin-10* . . . , May 4, 2004 109(17) pp. 2046-2049.

Matsuda, J. Biol. Chem., *Role of Adiponectin in Preventing Vascular Stenosis*, 277(40) pp. 37487-37491.

Motoshima, Biochem. Biophys. Res. Comm., *Adiponectin Suppresses Proliferation and Superoxide Generation and Enhances eNOS Activity* . . . , 204, 315, pp. 264-172.

Nakano, J. Biochem (Tokyo), *Isolation and Characterization of GBP28, a Novel Gelatin-Binding Protein Purified from Human Plazma*, Oct. 1996, 120(4), pp. 803-812.

Ohko, J. Biomed. Mat. Res. (Appl Biomet), *Self-Sterilizing and Self-Cleaning of Silicone Catheters Coated with $TiO_2$ Photocatalyst Thin Films: A Preclinical Work*, 58, 2001, pp. 97-101.

Ouichi, Circulation, *Adipocyte-derived Plasma Protein, Adiponectin, Suppresses Lipid Accumulation and Class A Scavenger Receptor Expression*, . . . 103(8), Feb. 27, 2001, p. 1057.

Ouichi, Circulation, *Novel Modulator for Endothelial Adhesion Molecules* . . . , 1999, 100, pp. 2473-2476.

Brakenhielm, PNAS, *Adiponectin-induced Antiangiogenesis and Antitumor Activity Involve Caspase-Mediated Enhothelial Cell Apoptosis*, 101(8), pp. 2476-2481.

Shanbhag, J. Biomed. Mar. Res., *Decreased Neutrophil Respiratory Burst on Exposure to Cobalt-Chrome alloy and Polystyrene in vitro*, vol. 26, 1992, pp. 185-195.

Shimada, Clin., Chim. Actga. *Adiponectin and Atherosclerotic Disease*, Jun. 2004, 344(1-2), pp. 1-12.

Singh, Nature, *A Component of Innate Immunity Prevents Bacterial Biofilm Development*, 417, May 30, 2002, pp. 552-555.

Talukder, J. Vet. Med. Sci. *Receptor-Mediated Transport of Lactoferin into the Cerebrospinal Fluid via Plasma in Young Calves,*, 65(9), 2003, pp. 957-964.

Taylor, Regul. Toxicol. Pharmacol. *Safety Determination for the use of Bovine Milk-derived Lactoferrin as a Component of an Antimicrobial Beef Carcass Spray*, Feb. 2004, 39(1), pp. 12-24.

Trampuz, et al., *Clin. Orthop, Molecular and Antibiofilm Approaches to Prosthetic Joint Infection*, (414), 2003, pp. 69-88.

Trif, Exp. Biol. Med (Maywood), *Liposomes as Possible Carriers for Lactoferrin in the Local Treatment of Inflammataory Diseases*, 226(6), 2001, pp. 559-564.

Tobinick, Swiss Med.Weekly, *Perispinal TNF-alpha Inhibition for Discogenic Pain*, 2003, 133, pp. 170-177.

Wulster-Radcliffe, Biochem, Biophys. Res. Comm., *Adiponectin Differentially Regulates Cytokines in Porcine Macrophages*, 316, 2004, pp. 924-929.

Yamamoto, Biochem. Biophys. Res. Comm., *Effect of Interleukin-10 on the Gene Expression of Type I Collagen, Fibronectin, and Decorin in Human Skin Fibroblasts: Differential Regulations by Transforming Growth Factor-β and Monocyte Chemoattractant Protein-1*, 316, 2004, pp. 924-929.

Yokota, Blood, *Adiponectin, a New Member of the Family of Soluble Defense Collagens, Negatively Regulates the Growth of Myelomonocytic Progenitors and the Functions of Macrophages*, Sep. 1, 2000, 96(5), pp. 1723-1732.

Brennen, Rheumatology, *Interleukin 10 and Arthritis*, 38, 1999, pp. 293-297.

Camody et al., Arthritis & Rheumatism, *Viral Interleukin-10 Gene Inhibition of Inflammation* . . . , 46(5), May 2002, pp. 1298-1308.

Goodman et al., JBMR, *Modulation of Bone Ingrowth and Tissue Differentiation by Local Infusion of Interleukin-10* . . . , 65A, 2003, pp. 43-50.

Hart et al., Immunology, *Comparison of the suppressive Effects of Interleukin-10 and Interleukin-4 on Synovial Fluid Macrophages and* . . . , 84(4), Apr. 1995, pp. 536-542.

Pollice et al., J. Orthop Res., *Interleukin-10 Inhibits Cytokine Synthesis in Monocytes Stimulated by Titanium Particles:* . . . , 16(6), Nov. 1998, pp. 697-704.

Trindade et al., Biomaterials, *Interleukin-10 Inhibits Polymethylmethacrylate Particle Induced Interleukin-6 and Tumor Necrosis* . . . , 22, 2001, pp. 2067-2073.

Hughes et al., Rheumatology, *Interleukin 10 and Arthritis*, 38, 1999, pp. 293-297.

Maeda, S. et al., Spine, *Changes with Age in Proteoglycan Synthesis in Cells Cultured in Vitro from the Inner and Outer Rabbit Annulus Fibrosus*, vol. 25(2), 2000, pp. 166-169.

Schierholz J M et al., "Development of A New CSF-Shunt with Sustained Release of An Antimicrobial Broad-Spectrum Combination", Zentralblatt fur Bakteriologie, Jun. 1997, pp. 107-123, vol. 286, No. 1, \* cited by examiner

AUTOLOGOUS COATINGS FOR IMPLANTS

This application claims the benefit of U.S. Provisional Patent Application Ser. No. 60/590,526, entitled "Intradiscal Anti-Inflammatory Therapy Involving Autologous Adiponectin", DiMauro et al., filed Jul. 23, 2004, and U.S. patent application Ser. No. 10/938,903, entitled "Intradiscal Anti-Inflammatory Therapy Involving Autologous Adiponectin", DiMauro et al., filed Sep. 10, 2004, and U.S. patent application Ser. No. 11/018,438, "Anti-Osteolytic Therapy Involving Adiponectin", DiMauro et al., filed Dec. 21, 2004, the specifications of which are incorporated by reference in its entirety.

BACKGROUND OF THE INVENTION

It is well known that infections occur in about 1% to about 5% of all primary arthroplasties, and that "the economic impact, the morbidity, and the emotional trauma of prosthetic joint infection is immense and devastating to the patient and society". Trampuz et al., *Clin. Orthop.*, (414), 2003 pp. 69–88. The costs associated with revision surgeries and prolonged hospital stays due to deep wound infection are significant.

Postoperative wound infection (deep and superficial) in spinal implant cases for scoliosis and cerebral palsy patients has a particularly high frequency. The majority of deep wound infections in spinal cases are treated by irrigation and debridement while leaving the wound open, allowing it to heal. However, removal of the hardware associated with deep wound infections in these cases is often necessary.

It is believed that a majority of these infections occur via transmission from microbes upon the surgical gloves, the patient's skin, implants or instruments. Unlike routine systemic infections, infections associated with implants ("periprosthetic infections") are particularly troublesome.

First, it has been reported that certain biomaterials cause an abnormal and inferior immune response. In short, a portion of the immune response is provided by the release of superoxide ions, such as hydroxyl radicals, that are lethal to microbes. However, when a periprosthetic infection occurs, it has been reported that biomaterials such as cobalt chrome alloys cause abnormal neutrophil activity, resulting in an inferior non-productive immune response. Shanbhag, *J. Biomed. Mar. Res.*, Vol. 26, 185–95, 1992.

Second, it appears that the presence of the implant surface helps the microbes survive both the immune response and antibiotic treatment. In particular, microbes of concern attach to the implant surface and form a polymer-like glaze (or "biofilm") between themselves and the local environment. This biofilm acts as an effective barrier to both neutrophils and antibiotics.

Although the periprosthetic infection itself is a primary concern for the patient, it is also known that the immune response triggered by the body to fight the infection also results in bone loss. In particular, the increased phagocyte concentration also increases the local concentration of tumor necrosis factor (TNF-α). The TNF-α concentration in turn upregulates the local level of osteoclasts. These increased osteoclast concentration uncouples the normal balance in bone metabolism, thereby leading to localized bone loss. This localized bone loss may result in the loosening of the implant, thereby necessitating its removal.

Prior art attempts at infection control have considered precoating spinal rods an intramedullary rods with an anti-infective coating. However, when the coatings at interconnection locations wear away, the space produced thereby leads to loose connections between the rod and the component to which it is connected.

In addition, prior art anti-infective coatings are typically cytotoxic to the microbes. This type of approach leads to building up resistance in the surviving microbes.

U.S. Pat. No. 6,503,507 ("Allen") discloses the use of a light-activated composition that produces singlet oxygen. Allen discloses that the singlet oxygen produced therefrom is effective in killing bacteria.

U.S. Pat. No. 6,527,759 ("Tachibana") discloses the use of light activated drugs that produce singlet oxygen.

Implant Sciences Corp. has promoted a surface treatment for percutaneous medical devices that prevents the growth of bacteria be employed the germ-fighting properties of silver coatings. U.S. Pat. No. 6,592,888 ("Jensen") discloses the use of metallic compounds in wound dressings to produce anti-microbial effects. U.S. Pat. No. 6,605,751 ("Gibbins") discloses the use of silver containing anti-microbial hydrophilic compositions. U.S. Patent Application 2003/0204229A1 ("Stokes") discloses the use of a polymeric casing containing cations as biologically active agents to be used on medical implants and devices.

Ohko, *J. Biomed. Mat. Res.* (*Appl Biomat*) 58: 97–101, 2001 reports coating titania upon silicone catheters and medical tubes, and illuminating those tubes with UV light. Ohko further reported the bactericidal effect of the subsequent photocatalysis on *E. coli* cells. However, Ohko states that $TiO_2$ is toxic under illumination, and that because the part of the $TiO_2$ coating buried in the patient's body can not be illuminated, the coating should not be harmful to the body. Therefore, it appears that Ohko discourages the in vivo irradiation of titania.

U.S. Published Patent Application 2003/0125679 ("Kubota") discloses a medical tube comprising an elastomer and a photocatalyst layer, wherein the tube is purported to have excellent antibacterial activity.

Hydrocephalus is a condition afflicting patients who are unable to regulate cerebrospinal fluid flow through their body's own natural pathways. Produced by the ventricular system, cerebrospinal fluid (CSF) is normally absorbed by the body's venous system. In a patient suffering from hydrocephalus, the cerebrospinal fluid is not absorbed in this manner, but instead accumulates in the ventricles of the patient's brain. If left untreated, the increasing volume of fluid elevates the patient's intracranial pressure and can lead to serious medical conditions such as subdural hematoma, compression of the brain tissue, dementia, impaired gait, and impaired blood flow.

The treatment of hydrocephalus has conventionally involved draining the excess fluid away from the ventricles and rerouting the cerebrospinal fluid to another area of the patient's body, such as the abdomen or vascular system. A drainage system, commonly referred to as a shunt, is often used to carry out the transfer of fluid. In order to install the shunt, typically a scalp incision is made and a small hole is drilled in the skull. A proximal, or ventricular, catheter is installed in the ventricular cavity of the patient's brain, while a distal, or drainage, catheter is installed in that portion of the patient's body where the excess fluid is to be reintroduced. To regulate the flow of cerebrospinal fluid and maintain the proper pressure in the ventricles, a pump or one-way control valve can be placed between the proximal and distal catheters. Such valves can comprise a ball-in-cone mechanism as illustrated and described in U.S. Pat. Nos. 3,886,948, 4,332,255, 4,387,715, 4,551,128, 4,595,390, 4,615,691, 4,772,257, and 5,928,182, all of which are hereby incorporated by reference. When properly functioning, these shunt systems provide an effective manner of regulating CSF in hydrocephalus patients.

After implantation and use over extended periods of time, these shunt systems tend to malfunction due to shunt occlusion. Frequently, the blockage occurs within the ventricular catheter. The obstruction can result from a number of problems, such as clotting, bloody CSF, excess protein content in the CSF, inflammatory or ependymal cells, brain debris, infection, or by choroid plexus or brain parenchyma in-growth through the openings of the ventricular catheter. Another potential cause of ventricular catheter occlusion is a condition known as slit ventricle syndrome in which the ventricular cavity collapses, thus blocking the openings of the ventricular catheter. If left untreated, the occlusion of the ventricular catheter can slow down and even prevent the ability of the shunt valve to refill, thereby rendering the shunt system ineffective.

In the past, the remedy for a clogged proximal catheter was to surgically remove and replace the catheter, which involved a risk of damage to the brain tissue or hemorrhage. The current trend is to rehabilitate the catheter in place through less invasive means. This can be accomplished in a procedure generally known as shunt or ventricular catheter revision which involves reaming the clogged catheter in its implanted state until the blockage is removed to thereby reestablish CSF flow through the ventricular catheter. Many shunt valves, such as the ones described in U.S. Pat. Nos. 4,816,016 and 5,176,627, are provided with a domed silicone reservoir that enables access to the attached ventricular catheter so that the system can be flushed out for this very reason. The self-sealing silicone dome can be pierced with a small needle to gain entry to the attached catheter, without affecting the ability of the dome to re-seal after the needle has been withdrawn. In some domed valves with right angle access, i.e., where the ventricular catheter extends at a 90 degree angle to the drainage catheter, a surgeon can gain entry to the clogged ventricular catheter percutaneously by inserting a rigid endoscopic instrument such as an endoscopic cutting tool or endoscopic electrode through the dome of the valve and straight down to the attached catheter. Thereafter, the obstruction can be cleared by cutting, cauterizing, or coagulating using the endoscopic instrument.

In addition, it is well known that infection is a well known complication associated with hydrocephalus shunts. It is well known that infections occur in about 5% to about 10% of all hydrocephalus shunt implantations. It is believed that a majority of these infections occur via transmission from microbes upon the surgical gloves, the patient's skin, implants or instruments. Unlike routine systemic infections, infections associated with implants ("periprosthetic infections") are particularly troublesome.

Therefore, it is an object of the present invention to provide an orthopedic implant and a hydrocephalus shunt adapted to prevent and/or treat occlusions and infections.

SUMMARY OF THE INVENTION

In a first aspect of the present invention, there is provided an orthopedic implant having an anti-infective, autologous coating. Preferably, the coating comprises at least one of a) lactoferrin, and b) transferrin.

In a second aspect of the present invention, there is provided a hydrocephalus shunt having an anti-inflammatory coating applied to at least the outside surface of the ventricular catheter. Preferably, the coating is a protein. More preferably, it comprises an effective amount of at least one of a) lactoferrin, b) transferrin, and c) adiponectin.

Each of the three anti-inflammatories has unique advantages:

I. Lactoferrin

There are four characteristics of lactoferrin that would make it a desirable as ant-inflammatory coating for a hydrocephalus shunt or an anti-infective coating for an orthopedic implant:

i. Anti-Inflammatory

Lactoferrin acts as an iron-binding anti-oxidant. Since iron is an important catalyst in the conversion of hydrogen peroxide and superoxide ions into the more potent hydroxyl radical, iron-binding agents prevent the generation of more potent oxidative species. This anti-oxidant property is expected to inhibit inflammation.

The literature has likewise reported the anti-inflammatory effects of lactoferrin. Guillen. *Arthritis. Rheum.*, 43, 2000, 2073–80 reports intra-articularly injecting 0.5–1 mg of lactoferrin into the knees of mice, reports significant suppression of local inflammation for up to 3 days, and concludes that lactoferrin is a potentially useful anti-inflammatory agent. Trif, *Exp. Biol. Med (Maywood)*, 226(6):559–64, 2001 reports intra-articularly injecting 20 ug/ml of lactoferrin into the knees of mice for the purpose of preventing arthritis induced inflammation. Hayashida, *J. Vet. Med. Sci.*, 66(2), 149–154, 2004 (Hayashida I) reports that injecting 30–100 mg/kg lactoferrin into adjuvant arthritis rats and finding that the lactoferrin injection suppressed both TNF-a (a pro-inflammatory) levels and the development of arthritis, while increasing IL-10 (an anti-inflammatory) levels.

ii. Analgesic

Importantly, Hayashida I also reported that the lactoferrin injection produced a very significant and dose-dependent analgesia. Hayashida, *Eur. J. Pharmacology*, 484, 2004, 175–181, reported that lactoferrin exerts an anti-nociceptive activity via potentiation of the peripheral u-opiodergic system.

Therefore, it appears that iron-binding agents are especially attractive for use with hydrocephalus shunts and orthopedic implants because they not only stop inflammation but they also may alleviate pain.

iii. Anti-microbial

Lactoferrin has well known anti-microbial qualities. In high concentrations, it is cytotoxic to pathogens. In sublethal concentrations, it is a bacteriostatic. Singh, *Nature*, 417, 30 May 2002, 552–555 postulates that the iron-binding quality of lactoferrin eliminates all available iron within the vicinity of the lactoferrin, thereby causing the microbes to wander across the surface of the implant instead of forming a biofilm.

Taylor, *Regul. Toxicol. Pharmacol.* 2004, February 39(1): 12–24 reported that bovine-milk derived lactoferrin (BMDL), an iron-binding glycoprotein known to be an effective natural anti-microbial, can be used as a spray applied electrostatcially, to raw beef caracases to detach bacteria adhereing to the surface in order to reduce microbial contamination. The use of BDML spray on beef caracses at a level of 0.2 ml per kg of beef was determined to be safe without the requirement of labeling of food products so treated. The two key components of this study were (1) a determination that exogenous lactoferrin exposure is in the range of existing background exposures of lactoferrin as a result of lactoferrin found naturally in beef, and (2) a determination that this potentially small increase in lactoferrin exposure is safe.

Therefore, it appears that coating a catheter, shunt or orthopedic implant with lactoferrin will have the effect of forcing the microbes to look elsewhere than the vicinity of the catheter for iron. Because they are bacteriostatic, the coatings of the present invention do not have the resistance problems associated with bacteriocidal coatings.

iv. Compatible with Brain Tissue

Lactoferrin (LF) is an endogenous compound that is present in abundant quantities in mother's milk. According to Talukder, *J. Vet. Med. Sci.*, 65(9), 2003, 957–64, LF easily passes the blood-brain barrier and is also present in CSF in significant amounts. It has also been speculated that lactoferrin plays a role in brain function. Therefore, the present invention as applied to hydrocephalus shunts merely supplements the endogenous amount of lactoferrin that is already present in CSF.

II. Transferrin

Transferrin is another iron-binding molecule that is produced autologous by the patient. It is expected that transferrin will behave comparably to lactoferrin.

i. Anti-Inflammatory

It is expected that transferrin will have anti-inflammatory properties that are comparable to lactoferrin. However, there have been some reports that transferrin may have pro-inflammatory qualities.

ii. Anti-microbial

It is expected that transferrin will have anti-microbial properties that are comparable to lactoferrin. Ardehali, *J. Biomed. Mat, Res.* 2003, Jul. 1, 66, 1, 21–28, reports that the inhibitory activity of human serum in preventing bacterial adhesion is mainly due to transferrin.

iii. Compatible with Brain Tissue

Since transferrin is manufactured in the choroid plexus portion of the brain, it is expected that the transferrin coating will have brain tissue compatibility.

iii. Autologous Source

Transferrin is present in human blood in very large quantities (~3 mg/ml). Since this concentration far exceeds the minimum levels thought to be required for its anti-inflammatory (~20 ug/ml) and anti-bacterial (~10 ug/ml) qualities, there is the potential for obtaining an effective amount of transferrin by simply concentrating it from the patient's own blood.

III. Adiponectin i. Anti-Inflammatory

Adiponectin (APN) has been shown to induce the production of several anti-inflammatory compounds (IL-10, TIMPs and IRAP) and suppress key pro-inflammatory compounds (TNF-α, IL-6) and reactive oxygen species.

According to Shimada, *Clin. Chim. Acta*, 2004, June 344(1–2):1–12, "Adiponectin has protective actions in the initiation and progression of atherosclerosis through anti-inflammatory and anti-atherosclerotic effects." According to Yokota, *Blood*, 1 Sep. 2000 96(5), 1723–1731, "All the data described here indicate that adiponectin is involved in the termination of inflammatory responses . . . Therefore, our observation . . . suggests that adiponectin may have therapeutic applications in diseases caused by excessive inflammatory responses." According to Diez, *Eur. J. Endocrinology* (2003) 148, 293–300, ". . . the ability of adiponectin to increase insulin sensitivity in connection with its anti-inflammatory and anti-atherogenic properties have made this novel adipocytokine a promising therapeutic tool for the future".

ii. Anti-Angiogenic

Matsuda , *J. Biol. Chem.*, 277(40) 37487–37491, reports that, in vitro, APN diminished DNA synthesis induced by growth factors such as PDGF, HB-EGF, and bFGF, and smooth muscle cell proliferation and migration. Matsuda concludes that increasing plasma APN levels should be useful in preventing vascular restenosis. Brakenhielm, *PNAS*, 101(8), 2476–81, reports that APN potently inhibits endothelial cell proliferation and migration and remarkably prevented new blood vessel growth. Brakenhielm concludes that APN is a negative regulator of angiogensis and is a direct endogenous angiogenesis inhibitor.

Since tissue growth requires angiogenesis, it appears that the anti-angiogenic properties of APN would make it a useful compound for preventing tissue in-growth into the hydrocephalus shunt and other medical devices or implants susceptible to tissue in-growth.

iii. Anti-Adhesion

Ouchi, *Circulation*, 1999, 100, 2473–76, reports that physiological concentrations of APN dose-dependently significantly suppressed TNF-a mediated expression of adhesion molecules in human aortic endothelial cells, and concludes that physiological concentrations of APN regulate endothelial cells in response to inflammatory stimuli.

Since tissue in-growth requires cell adhesion to the substrate wall, it appears that the anti-adhesion properties of APN would make it a useful compound for preventing tissue in-growth into the hydrocephalus shunt and other medical devices or implants susceptible to tissue in-growth.

Moreover, since it is believed that significant pain is caused by scar tissue formation associated with adhesion of implants to surrounding tissue, it is likewise believed that application of adiponectin to spinal implants will have the effect of reducing adhesion formation and therefore reducing pain.

iv. Autologous Source

Adiponectin is a hormone present in human plasma (0.01%, or 5–10 ug/ml)—a level 1000X more than any other hormone. Since this endogenous concentration is comparable with the minimum levels thought to be required for its anti-inflammatory 5 ug/ml) and anti-adhesion (5–25 ug/ml) qualities, there is the potential for obtaining APN by simply concentrating it from the patient's own blood.

DETAILED DESCRIPTION OF THE INVENTION

In some embodiments, the orthopedic implant upon which the coating is coated is a spinal implant. Preferred spinal implants include motion implants, fusion implants and fixation implants. Preferred motion implants include lumbar motion discs, cervical motion discs and posterior dynamic stabilization devices. Preferred fusion implants include ALIF, TLIF and PLIF cages, and ALIF, TLIF and PLIF mesh. Preferred fixation implants includes components (such as hooks, rods, and screws), and systems (such as scoliosis correction systems).

In some embodiments, the orthopedic implant is a hip implant. Preferred implants include modular head and femoral components, and acetabular cups.

In some embodiments, the orthopedic implant is a hip implant. Preferred implants include modular tibial and femoral components.

The coatings of the present invention have special advantage because, in some embodiments, they can be produced autologously in the operating theatre and then applied in vivo to an already-assembled system (such as a rod and screw spinal fixation system, or such as a modular hip or knee). Accordingly, the present invention avoids the loose connections problems associated with pre-coated rods discussed above. The coating may be sprayed upon the assembled implant either before the assembled implant is implanted or after the assembled implant is implanted.

Therefore, in accordance with the present invention, there is provided a method of treating an implant comprising the steps of:
- a) providing an unassembled implant comprising a first component and a second component,
- b) assembling the implant in the patient's body, and
- c) spraying a coating upon a surface of the assembled implant.

In some embodiments, the coating is provided in a container and dispersed as an aerosol spray. In other embodiments, the coating is a plasma-based formulation comprising fibrinogen, and is combined with thrombin and dispersed as a spray, or via a fibrin glue gun.

Therefore, in accordance with the present invention, there is provided a method of treating an implant, comprising the steps of:
- a) providing an implant, and
- b) spraying a coating upon the implant, wherein the coating contains an effective amount of a compound selected from the group consisting of lactoferrin, transferrin and adiponectin.

In one embodiment, the source of these preferred anti-inflammatory molecules (AIM) is exogenous. In this embodiment, the AIM can be lyophilized and provided to the surgeon in a vial as a dried powder. It can be then reconstituted by the surgeon at the point of care and mixed with autologous fibrin glue or any other suspension medium. The mixture can then be applied to the implant surface (such as the outside of the ventricular catheter or a spinal rod) as a thin coating prior to catheter insertion.

In another embodiment, as discussed above, the AIM is derived from the patient's own blood (i.e., it's autologous).

In some embodiments, the anti-inflammatory can be delivered post-operatively. In some shunt embodiments, a short needle is inserted into the ventricular catheter until its distal end approaches the proximal inlet hole of the ventricular catheter. Once this position is reached, a saline solution containing the AIM is injected into the catheter until the solution emerges from the inlet holes. This method allows both the catheter and the region surrounding the catheter to be filled with an effective amount of the AIM. In some embodiments, the delivery needle has predetermined holes therein to correspond with the holes of the ventricular catheter.

In some embodiments, the iron-binding agent (lactoferrin or transferrin) is provided exogenously. Preferably, the exogenous iron-binding agent is a recombinant iron-binding agent. More preferably, human apo-transferrin (20 mg/ml) is obtainable from Sigma, Poole, UK; exogenous iron-free lactoferrin is obtainable from is obtainable from Sigma Chemical (St. Louis, Mo.); and recombinant lactoferrin is obtainable from is obtainable from Tatua (Morrinsville, NZ).

In some embodiments, the iron-binding agent is derived autologously (i.e., from the patient). When the iron binding agent is transferrin, the iron-binding agent is preferably derived from the serum or plasma of the patient. In some embodiments thereof, autologous serum is used as the formulation comprising an effective amount of tranferrin (as it contains about 3 mg/ml of transferrin). In others, the autologous serum undergoes at least partial purification to concentrate the transferrin prior to its administration. When the iron binding agent is lactoferrin, it is preferably derived from white blood cells present in the buffy coat of the patient's blood.

In some embodiments, the autologously derived iron-binding agent is purified by and eluted from an antibody, preferably a monoclonal antibody. For example, in one preferred embodiment, transferrin and its antibody (CD71) are allowed to complex, and the complex is captured by immobilized IgG, as in Desai, *Anal. Biochem.* 2004, May 15, 328(2) 162–5.

In some embodiments, autologous adiponectin is obtained via the methods disclosed in U.S. Provisional Patent Application Ser. No. 60/590,526, entitled "Intradiscal Anti-Inflammatory Therapy Involving Autologous Adiponectin", DiMauro et al., filed Jul. 23, 2004, and U.S. patent application Ser. No. 10/938,903, entitled "Intradiscal Anti-Inflammatory Therapy Involving Autologous Adiponectin", DiMauro et al., filed Sep. 10, 2004, the specifications of which are incorporated by reference in its entirety.

Briefly, in some embodiments, there is provided a method of treating a hydrocephalus shunt or orthopedic implant, wherein a formulation consisting essentially of plasma comprising an effective amount of APN is coated upon an outer surface of the shunt or implant. In some embodiments thereof, an APN-rich portion of the plasma is obtained, for example, by using a gradient fluid with a centrifuge, and then coating that APN-rich fraction onto the shunt or orthopedic implant outer surface.

In some embodiments, the plasma may be centrifuged in a container having a plurality of side ports. A needle may be passed through one of these side ports to access the APN-rich layer of the plasma.

In some embodiments, the plasma portion is separated from the remainder of the blood and passed through an affinity column containing a separation material for which APN has a high affinity. The APN is thus preferentially adsorbed onto the separation material. Next, adsorbed APN is eluted from the separation material using a suitable elution solution.

Nakano, *J. Biochem (Tokyo)*, 1996 October 120(4) 803–12, examined methods for isolating APN, and found not only that APN binds specifically to gelatin, but also that it can be eluted from the gelatin material by a 1M NaCl solution. Nakano further reported that applying these methods to 500 ml of human plasma resulted in the isolation of about 50 µg of APN.

Therefore, in preferred embodiments, the plasma portion is separated from the remainder of the blood and passed through an affinity column containing gelatin (or collagen I, III or V), and the adsorbed APN is eluted from the column using a 1 M NaCl solution.

In other embodiments, APN may be separated from the collagen by digesting the collagen with, for example, trypsin or collagenase.

In other embodiments, APN is obtained from adipose tissue, as it is exclusively released by adipose tissue.

In other embodiments, other conventional separation procedures may be used to separate APN from the other components of whole blood or fat.

Conventional protein production technology may be exploited to include a number of unit processes designed to partially purify the concentration of APN. Such conventional processes include the use of glass beads to capture the APN; the use of a 10 kD filter to capture the APN; the use of a molecular sieve to dewater the plasma; the use of ammonium sulfate to precipitate out the APN; and the use of ethanol extraction to precipitate out the APN.

It is reasonable to expect that adoption of at least one of the partial purification techniques described above will lead to a 5–10 fold increase in the APN concentration in the partially purified solution.

In some embodiments, monoclonal antibodies may be used to separate the adiponectin from the rest of the plasma.

It is believed that as little as about 5 μg/ml APN is an effective anti-inflammatory concentration. Greater amounts are generally believed to produce greater anti-inflammatory effects.

Accordingly, in some embodiments of the present invention, the formulation comprises at least 5 μg APN/ml, preferably the formulation comprises at least 10 μg APN/ml, more preferably at least 20 μg/ml, and more preferably at least 30 μg APN/ml.

In some embodiments, the APN or induced cells may be combined with a sustained release device in order to insure a continued presence of the APN in the implant region. In some embodiments, autologous cryoprecipitated fibrinogen is used to make the sustained release device. Cryoprecipated fibrin may be used as a carrier for APN. In one embodiment, cryoprecipitated fibrinogen is taken from the patient's blood (that could be donated before surgery or even collected during surgery with a Cell-Saver). With autologous fibrin, there would be no risk of rejection since the fibrin is from the patient's own blood proteins. The addition of thrombin to the cryoprecipitate creates a stable gel. With time, the cryoprecipitated fibrin may be replaced with a fibrocartilage-like material, similar to that of the host tissue.

It is noted by the inventors that since adiponectin has a high affinity for gels, and since fibrin may be made in a gel form, adiponectin may very well have a high affinity for a fibrin gel. Accordingly, in some embodiments, the fibrin gel made from cryoprecipitated fibrinogen is used as an affinity substrate for concentrating adiponectin. In some embodiments thereof, the fibrin gel is made from combining cryoprecipitated fibrinogen and thrombin and then formed into a sheet-like geometry, and the plasma portion of the patient's blood is flowed across the sheet. The adiponectin in the plasma should bind to the gel. Thereafter, the adiponectin may be eluted from the gel by a NaCl-containing solution.

In some embodiments of the present invention, the protein isolation technology disclosed in U.S. Ser. No. 10/977,858, "Intraoperative Method for Isolating and Concentrating Autologous Growth Factors", Kapur et al., filed Oct. 29, 2004, the specification of which is incorporated by reference herein in its entirety, is used to concentrate either the adiponectin, transferrin or lactoferrin. In the case of adiponectin, a commercially-available antibody with a high affinity for adiponectin is featured on the affinity column. The same steps disclosed in Kapur et al. are carried out to separate out the other factors in the blood to arrive at a concentrated solution of adiponectin.

In the case of transferrin, a commercially-available antibody to either transferrin or its corresponding cell receptor may be used. The same steps disclosed in Kapur et al. are carried out to separate out the other factors in the blood to arrive at a concentrated solution of transferrin. In preferred embodiments, the affinity column contains the antibody to the transferrin protein (as opposed to its receptor).

In the case of lactoferrin, it is possible that this molecule is bound to the surface of white blood cells rather than freely circulating in the plasma. If this is so, then the clinician could add an agent to the pertinent chamber of the Kapur et al. device in addition to or in lieu of a degranulation agent in order to evoke a release of the lactoferrin from the white blood cells. Then, the clinician uses an affinity column with an antibody to lactoferrin to obtain a concentrate.

Also in accordance with the present invention, there is provided a method of treating a hydrocephalus shunt, comprising administering an effective amount of a formulation comprising a APN and fibrin glue having a fibrinogen concentration of at least 10 mg/ml onto a hydrocephalus shunt, preferably at least 20 mg/ml.

Therefore, in some embodiments, there is provided a kit for treating a hydrocephalus shunt, comprising:
 a) a hydrocephalus shunt, and
 b) a formulation comprising an effective amount of adiponectin effective for coating the shunt.

In some embodiments, adjunct materials disclosed in U.S. patent application Ser. No. 10/631,487, filed Jul. 31, 2003, "Transdiscal Administration of Specific Inhibitors of p38 Kinase" (DEP5144), the specification of which is incorporated by reference in its entirety, are provided along with the APN.

Furthermore, it should be appreciated by one skilled in the art that any number of medical devices or implants may benefit by having the coatings of this invention incorporated therewith to enhance the function and/or life of the device or implant. For example, intraocular lenses, placed to restore vision after cataract surgery is often compromised by the formation of a secondary cataract. The latter is often a result of cellular overgrowth on the lens surface and can be potentially minimized by coatings of this invention manifesting anti-angiogenic characteristics. Other medical devices which often fail due to tissue in-growth or accumulation of proteinaceous material in, on and around the device, such as stents, dialysis grafts, colostomy bag attachment devices, ear drainage tubes, leads for pace makers and implantable defibrillators can also benefit from the coatings of this invention. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using coatings of this invention. Essentially, any type of medical device may be coated in some fashion with coatings of this invention which enhance treatment over use of the singular use of the device or implant.

We claim:

1. A hydrocephalus shunt having a ventricular catheter wherein adiponectin is present as a coating upon an outer surface of the catheter.

2. The shunt of claim 1 wherein the adiponectin coating is autologous.

3. A hydrocephalus shunt having a ventricular catheter having an outer surface having an anti-microbial coating thereon comprising transferrin.

4. The shunt of claim 3 wherein the transferrin coating is autologous.

5. A kit for treating a hydrocephalus shunt, comprising:
 a) a hydrocephalus shunt, and b) a formulation comprising an effective amount of an anti-inflammatory coating effective for coating the shunt, wherein the coating is adiponectin.

6. The kit of claim 5 wherein the adiponectin coating is autologous.

7. An orthopedic implant having an outer surface having a protein-based, anti-inflammatory coating thereon comprising adiponectin.

8. The implant of claim 7 wherein the anti-inflammatory coating is adiponectin.

9. The implant of claim 8 wherein the adiponectin coating is autologous.

10. The implant of claim 7 wherein the implant is a spinal implant.

11. The implant of claim 10 wherein the spinal implant is selected from the group consisting of a motion implant, a fusion implant and a fixation implant.

12. The implant of claim 11 wherein the spinal implant is a motion implant selected from the group consisting of a lumbar motion disc, a cervical motion disc and a posterior dynamic stabilization device.

13. The implant of claim 11 wherein the spinal implant is a fusion implant selected from the group consisting of a cage and a mesh.

14. The implant of claim 11 wherein the spinal implant is a fixation implant selected from the group consisting of a hook, a rod, a screw, and a scoliosis correction system.

15. The implant of claim 7 wherein the orthopedic implant is a hip implant selected from the group consisting of a modular head, a modular femoral component, and an acetabular cup.

16. The implant of claim 7 wherein the orthopedic implant is a knee implant selected from the group consisting of a tibial component and a femoral component.

17. A method of coating an implant comprising the steps of:
 a. providing an unassembled implant,
 b. assembling the implant in the patient's body, and
 c. spraying a coating upon a surface of the assembled implant.

18. A method of treating an implant, comprising the steps of:
 a. providing an implant, and
 b. spraying a coating upon the implant, wherein the coating contains an effective amount of a compound selected from the group consisting of, transferrin and adiponectin.

19. The method of claim 18 wherein the coating is sprayed upon the implant before implantation.

20. The method of claim 18 wherein the coating is sprayed upon the implant after implantation.

* * * * *